(12) United States Patent
Bej et al.

(10) Patent No.: US 11,708,543 B2
(45) Date of Patent: Jul. 25, 2023

(54) ITACONATE SURFACTANTS

(71) Applicant: Conopco Inc., Englewood Cliffs, NJ (US)

(72) Inventors: Sujoy Bej, Bangalore (IN); Nivedita Jagdish Patil, Bangalore (IN); Saheli Chakraborty, Bangalore (IN); Sumana Roychowdhury, Bangalore (IN); Ramakrishnan Subramanian, Bangalore (IN)

(73) Assignee: Conopco Inc.

( * ) Notice: Subject to any disclaimer, the term of this patent is extended or adjusted under 35 U.S.C. 154(b) by 131 days.

(21) Appl. No.: 17/420,148

(22) PCT Filed: Jan. 6, 2020

(86) PCT No.: PCT/EP2020/050148
§ 371 (c)(1),
(2) Date: Jul. 1, 2021

(87) PCT Pub. No.: WO2020/144144
PCT Pub. Date: Jul. 16, 2020

(65) Prior Publication Data
US 2022/0049187 A1 Feb. 17, 2022

(30) Foreign Application Priority Data
Jan. 8, 2019 (EP) .................... 19150712

(51) Int. Cl.
*C11D 1/74* (2006.01)
*C11D 3/37* (2006.01)
*C07C 69/593* (2006.01)
*C11D 11/00* (2006.01)

(52) U.S. Cl.
CPC ............ *C11D 1/74* (2013.01); *C11D 11/0017* (2013.01)

(58) Field of Classification Search
CPC ....... C11D 1/74; C11D 3/3707; C11D 3/3715; C11D 11/0017; C07C 69/593
See application file for complete search history.

(56) References Cited

FOREIGN PATENT DOCUMENTS

| WO | WO 2011/109047 | * | 9/2011 | ............ C07C 309/12 |
| WO | WO2012061092 | | 5/2012 | |

OTHER PUBLICATIONS

Chakraborty et al.; Amphilphilic Double-Brush Polymers Based on Itaconate Diesters; Macromolecules; Jan. 1, 2017; pp. 5004-5013; vol. 50, No. 13; India.

* cited by examiner

*Primary Examiner* — Brian P Mruk
(74) *Attorney, Agent, or Firm* — N.V. Nederlandsch Octrooibureau

(57) ABSTRACT

The invention provides an itaconate surfactant having the following formula (I)

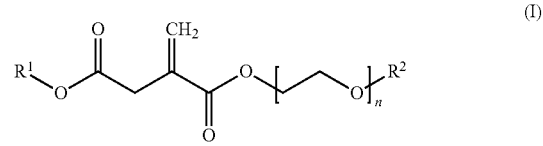

in which $R^1$ is selected from aliphatic hydrocarbyl groups having 4 to 22 carbon atoms; $R^2$ is selected from hydrogen and aliphatic hydrocarbyl groups having 1 to 4 carbon atoms; and n is an integer ranging from 8 to 20.

The surfactants of the invention are benign to the skin and to the environment yet can offer a performance that is comparable to that of "traditional" anionic and anionic/nonionic surfactant systems, especially on difficult-to-remove stains.

7 Claims, No Drawings

ITACONATE SURFACTANTS

FIELD OF THE INVENTION

The present invention relates to novel itaconate surfactants and their applications.

BACKGROUND AND PRIOR ART

Anionic sulfonate or sulfate surfactants, for example linear alkylbenzene sulfonate (LAS) or primary alcohol sulfate (PAS), are often used as the principal detergent-active ingredients in household detergent compositions because of their excellent cleaning properties. They are frequently used in conjunction with ethoxylated alcohol nonionic surfactants which give improved detergency on hydrophobic soils.

The above anionic and anionic/nonionic surfactant systems are robust and highly efficient on a wide range of soils and under a wide range of conditions, for example, temperature and water hardness. However, the anionic surfactants are not noted for mildness to skin. Furthermore, their manufacture is still heavily reliant on non-renewable resources, such as petroleum, natural gas, and coal.

The problem underlying the present invention is to provide surfactants and surfactant systems which are benign to the skin and to the environment yet can offer a performance that is comparable to that of "traditional" anionic and anionic/nonionic surfactant systems, especially on difficult-to-remove stains. Such stains include, for example, polyphenolic-based stains such as cherry juice, blueberry juice and red wine, along with tea, coffee and chocolate pudding.

This problem is solved by providing the surfactant according to the present invention.

SUMMARY OF THE INVENTION

The surfactant according to the present invention is an itaconate surfactant having the following formula (I)

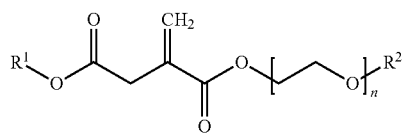

(I)

in which $R^1$ is selected from aliphatic hydrocarbyl groups having 4 to 22 carbon atoms; $R^2$ is selected from hydrogen and aliphatic hydrocarbyl groups having 1 to 4 carbon atoms; and n is an integer ranging from 8 to 20.

The invention also provides a process for making the itaconate surfactant of formula (I), the process comprising the steps of:
(i) reacting itaconate anhydride with an alcohol of the general formula $R^1OH$ (in which $R^1$ is as defined above) to yield an itaconate ester; and
(ii) ethoxylating the itaconate ester to produce the itaconate surfactant of formula (I).

DETAILED DESCRIPTION AND PREFERRED EMBODIMENTS

In formula (I) above, $R^1$ is preferably selected from linear or branched, saturated or unsaturated hydrocarbyl groups having from 8 to 20 carbon atoms and from 0 to 3 double bonds. More preferably, $R^1$ is selected from linear alkyl or linear alkenyl groups containing from 12 to 18 carbon atoms and 0 or 1 double bond. Preferred examples of such groups include lauryl, myristyl, palmityl, cetyl, oleyl and stearyl and mixtures thereof (as may typically be derived from natural fats and/or optionally hydrogenated natural oils such as coconut oil, palm kernel oil or tallow).

In formula (I) above, $R^2$ is preferably methyl, ethyl, or n-butyl and more preferably methyl.

In formula (I) above, n preferably ranges from 8 to 10 and is more preferably 8 or 9.

A preferred process for making the itaconate surfactant of formula (I) comprises the steps of:
(i) reacting itaconate anhydride with an alcohol of the general formula $R^1OH$ (in which $R^1$ is as defined above) to yield an itaconate ester;
(iia) reacting polyethylene glycol of the formula $R^2O$—$(CH_2CH_2O)_n$—$CH_2CH_2OH$ (in which $R^2$ and n are as defined above) with a sulfonyl halide, to form an intermediate; and
(iib) reacting the itaconate ester obtained in (i) with the intermediate obtained in (iia) to produce the itaconate surfactant of formula (I).

The sulfonyl halide in (iia) may suitably be selected from aromatic sulfonyl halides in which the aromatic group may be a benzene or naphthalene nucleus having 0, 1 or 2 substituents (which are each independently selected from halogen atoms and $C_{1-4}$ alkyl groups), with the bond to the sulfonyl group extending from the nucleus. The aromatic group is preferably a benzene nucleus which may be substituted with a chlorine atom or a methyl group, more preferably in the 4-position. Examples of preferred aromatic sulfonyl halides include benzenesulfonyl chloride, 4-chlorobenzenesulfonyl chloride and especially 4-toluenesulfonyl chloride. Other sulfonyl halides that can be used include $C_{1-4}$ alkanesulfonyl halides such as methane- and ethane-sulfonyl chloride and bromide.

The itaconate surfactants of the invention are useful in a variety of end use applications including general purpose detergency, including laundry and hard surface cleaner applications.

The invention accordingly includes detergent compositions including the itaconate surfactants of the invention, methods of cleaning using detergent compositions including the itaconate surfactants of the invention; and the use of the itaconate surfactants of the invention as detergents.

In laundry applications, the itaconate surfactants of the invention will typically be formulated together with other ingredients into a laundry detergent composition.

The invention accordingly includes laundry detergent compositions including the itaconate surfactants of the invention, methods of cleaning laundry using laundry detergent compositions including the itaconate surfactants of the invention; and the use of the itaconate surfactants of the invention as detergents in laundry washing.

The term "laundry detergent composition" in the context of this invention denotes formulated compositions intended for and capable of wetting and cleaning domestic laundry such as clothing, linens and other household textiles. The term "linen" is often used to describe certain types of laundry items including bed sheets, pillow cases, towels, tablecloths, table napkins and uniforms. Textiles can include woven fabrics, non-woven fabrics, and knitted fabrics; and can include natural or synthetic fibres such as silk fibres, linen fibres, cotton fibres, polyester fibres, polyamide fibres such as nylon, acrylic fibres, acetate fibres, and blends thereof including cotton and polyester blends.

Examples of laundry detergent compositions include heavy-duty detergents for use in the wash cycle of automatic washing machines, as well as fine wash and colour care detergents such as those suitable for washing delicate garments (e.g. those made of silk or wool) either by hand or in the wash cycle of automatic washing machines.

A laundry detergent composition according to the invention may suitably be in liquid or particulate form, or a mixture thereof.

The term "particulate" in the context of this invention denotes free-flowing or compacted solid forms such as powders, granules, pellets, flakes, bars, briquettes or tablets.

One preferred form for a particulate laundry detergent composition according to the invention is a free-flowing powdered solid, with a loose (unpackaged) bulk density generally ranging from about 200 g/l to about 1,300 g/l, preferably from about 400 g/l to about 1,000 g/l, more preferably from about 500 g/l to about 900 g/l.

The laundry detergent composition according to the invention is most preferably in liquid form.

The term "liquid" in the context of this invention denotes that a continuous phase or predominant part of the composition is liquid and that the composition is flowable at 15° C. and above. Accordingly, the term "liquid" may encompass emulsions, suspensions, and compositions having flowable yet stiffer consistency, known as gels or pastes. The viscosity of the composition may suitably range from about 200 to about 10,000 mPa·s at 25° C. at a shear rate of 21 sec$^{-1}$. This shear rate is the shear rate that is usually exerted on the liquid when poured from a bottle. Pourable liquid compositions generally have a viscosity of from 200 to 2,500 mPa·s, preferably from 200 to 1500 mPa·s.

Liquid compositions which are pourable gels generally have a viscosity of from 1,500 mPa·s to 6,000 mPa·s, preferably from 1,500 mPa·s to 2,000 mPa·s.

The itaconate surfactant of the invention will generally be included in the laundry detergent composition according to the invention at a level of 0.5 to 35% (by weight based on the total weight of the composition).

A laundry detergent composition according to the invention will generally include further surfactants (in addition to the itaconate surfactant of the invention). The choice of surfactant, and the total amount present, will depend on the intended mode of use. For example, different surfactant systems may be chosen for hand-washing products and for products intended for use in different types of automatic washing machine. In compositions for machine washing of fabrics, a total surfactant amount of from 5 to 40%, such as 15 to 35% (by weight based on the total weight of the composition) is generally appropriate. Higher levels may be used in compositions for washing fabrics by hand, such as up to 60% (by weight based on the total weight of the composition.

Further surfactants (in addition to the itaconate surfactant of the invention) may suitably be selected from non-soap anionic surfactants, which are typically salts of organic sulfates and sulfonates having alkyl radicals containing from about 8 to about 22 carbon atoms, the term "alkyl" being used to include the alkyl portion of higher acyl radicals. Examples of such materials include alkyl sulfates, alkyl ether sulfates, alkaryl sulfonates, alpha-olefin sulfonates and mixtures thereof. The alkyl radicals preferably contain from 10 to 18 carbon atoms and may be unsaturated. The alkyl ether sulfates may contain from one to ten ethylene oxide or propylene oxide units per molecule, and preferably contain one to three ethylene oxide units per molecule. The counterion for anionic surfactants is generally an alkali metal such as sodium or potassium; or an ammoniacal counterion such as monoethanolamine, (MEA) diethanolamine (DEA) or triethanolamine (TEA).

Mixtures of any of the above described materials may also be used.

In a laundry detergent composition according to the invention, the total level of non-soap anionic surfactant may suitably range from 5 to 30% (by weight based on the total weight of the composition).

Further surfactants (in addition to the itaconate surfactant of the invention) may also be selected from nonionic surfactants, which are typically aliphatic $C_8$ to $C_{18}$, more preferably $C_{12}$ to $C_{15, primary}$ linear alcohol ethoxylates with an average of from 3 to 20, more preferably from 5 to 10 moles of ethylene oxide per mole of alcohol. Also suitable are sugar-derived nonionic surfactants such as alkyl polyglycosides corresponding to the general formula $R_1O(R_2O)_b(Z)_a$ in which $R_1$ is a monovalent hydrocarbyl group having from 6 to 30 carbon atoms; $R_2$ is a divalent alkylene radical having from 2 to 4 carbon atoms; Z is a saccharide (preferably glucose) residue having 5 or 6 carbon atoms; b is a number having a value from 0 to 12 (preferably 0) and a is a number having a value from 1 to 6. Good results have been obtained with polysorbate-based non-ionic surfactants such as ethoxylates of sorbitol esters of fatty acids having the following core structure:

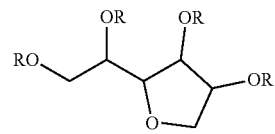

in which each R is independently selected from hydrogen or a PEG chain with or without a fatty ester end-cap. Typical materials have the following structure:

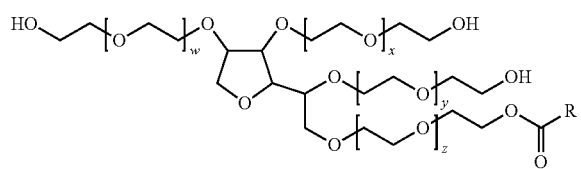

where w+x+y+z ranges from 3 to 30 and R is a monovalent hydrocarbyl group having from 6 to 30 carbon atoms. Preferably w+x+y+z is 4, 5, or 20; and R is selected from linear alkyl or linear alkenyl groups containing from 12 to 18 carbon atoms and 0 or 1 double bond, such as lauryl, myristyl, palmityl, cetyl, oleyl and stearyl and mixtures thereof (as may typically be derived from natural fats and/or optionally hydrogenated natural oils such as coconut oil, palm kernel oil or tallow). Examples of such materials include polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (4) sorbitan monolaurate, polyoxyethylene (4) sorbitan monostearate, and polyoxyethylene (5) sorbitan monooleate.

Mixtures of any of the above described materials may also be used.

In a laundry detergent composition according to the invention, the total level of nonionic surfactant (in addition to the itaconate surfactant of the invention) may suitably range from 0 to 25% (by weight based on the total weight of the composition).

A liquid laundry detergent composition according to the invention may generally comprise from 5 to 95%, preferably from 10 to 90%, more preferably from 15 to 85% water (by weight based on the total weight of the composition). The composition may also incorporate from 0.1 to 15% (by weight based on the total weight of the composition) of non-aqueous carriers such as hydrotropes, co-solvents and phase stabilizers.

A laundry detergent composition according to the invention may contain one or more builders. Builders enhance or maintain the cleaning efficiency of the surfactant, primarily by reducing water hardness. This is done either by sequestration or chelation (holding hardness minerals in solution), by precipitation (forming an insoluble substance), or by ion exchange (trading electrically charged particles).

Builders for use in the invention can be of the organic or inorganic type, or a mixture thereof. Non-phosphate builders are preferred.

Preferred inorganic, non-phosphate builders for use in the invention may be selected from zeolites, sodium carbonate, 6-sodium disilicate and mixtures thereof.

Preferred organic, non-phosphate builders for builders for use in the invention may be selected from polycarboxylates (e.g. citrates) in acid and/or salt form and mixtures thereof.

Mixtures of any of the above described materials may also be used.

The overall level of builder, when included, may range from about 0.1 to about 80%, preferably from about 0.5 to about 50% (by weight based on the total weight of the composition).

A particulate laundry detergent composition of the invention may include one or more fillers to assist in providing the desired density and bulk to the composition. Preferred fillers for use in the invention include alkali metal (more preferably sodium and/or potassium) sulfates and chlorides and mixtures thereof, with sodium sulfate and/or sodium chloride being most preferred. Filler, when included, may be present in a total amount ranging from about 1 to about 80%, preferably from about 5 to about 50% (by weight based on the total weight of the composition).

A laundry detergent composition according to the invention may include one or more polymeric cleaning boosters such as antiredeposition polymers, soil release polymers and mixtures thereof.

Anti-redeposition polymers stabilise the soil in the wash solution thus preventing redeposition of the soil. A preferred material is ethoxylated polyethyleneimine, with an average degree of ethoxylation being from 10 to 30, preferably from 15 to 25 ethoxy groups per ethoxylated nitrogen atom in the polyethyleneimine backbone. Another type of suitable anti-redeposition polymer for use in the invention includes cellulose esters and ethers, for example sodium carboxymethyl cellulose.

Mixtures of any of the above described materials may also be used.

The overall level of anti-redeposition polymer, when included, may range from 0.05 to 6%, more preferably from 0.1 to 5% (by weight based on the total weight of the composition).

Soil release polymers (SRPs) help to improve the detachment of soils from fabric by modifying the fabric surface during washing. The adsorption of a SRP over the fabric surface is promoted by an affinity between the chemical structure of the SRP and the target fibre. Preferred SRPs for use in the invention include copolyesters formed by condensation of terephthalic acid ester and diol, preferably 1,2 propanediol, and further comprising an end cap formed from repeat units of alkylene oxide capped with an alkyl group.

Mixtures of any of the above described materials may also be used.

The overall level of SRP, when included, may range from 0.1 to 10%, preferably from 0.3 to 7%, more preferably from 0.5 to 5% (by weight based on the total weight of the composition).

A laundry detergent composition according to the invention may in some cases contain one or more fatty acids and/or salts thereof. Preferred examples of such materials include saturated C12-18 fatty acids such as lauric acid, myristic acid, palmitic acid or stearic acid; and fatty acid mixtures in which 50 to 100% (by weight based on the total weight of the mixture) consists of saturated C12-18 fatty acids. Such mixtures may typically be derived from natural fats and/or optionally hydrogenated natural oils (such as coconut oil, palm kernel oil or tallow). The fatty acids may be present in the form of their sodium, potassium or ammonium salts and/or in the form of soluble salts of organic bases, such as mono-, di- or triethanolamine.

Mixtures of any of the above described materials may also be used.

Fatty acids and/or their salts, when included, may be present in an amount ranging from about 0.25 to 5%, more preferably from 0.5 to 5%, most preferably from 0.75 to 4% (by weight based on the total weight of the composition).

For formula accounting purposes, in the formulation, fatty acids and/or their salts (as defined above) are not included in the level of surfactant or in the level of builder.

A liquid laundry detergent composition according to the invention may comprise one or more rheology modifiers. Examples of such materials include polymeric thickeners, such as hydrophobically modified alkali swellable emulsion (HASE) copolymers; and/or structurants which form a network within the composition, such as hydrogenated castor oil, microfibrous cellulose and citrus pulp fibre.

A laundry detergent composition according to the invention may comprise an effective amount of one or more enzymes selected from the group comprising, pectate lyase, protease, amylase, cellulase, lipase, mannanase and mixtures thereof. The enzymes are preferably present with corresponding enzyme stabilizers.

A liquid laundry detergent composition according to the invention preferably has a pH in the range of 5 to 9, more preferably 6 to 8, when measured on dilution of the composition to 1% (by weight based on the total weight of the composition) using demineralised water.

A laundry detergent composition of the invention may contain further optional ingredients to enhance performance and/or consumer acceptability. Examples of such ingredients include fragrance oils, foam boosting agents, preservatives (e.g. bactericides), antioxidants, sunscreens, anticorrosion agents, colorants, pearlisers and/or opacifiers, and shading dye. Each of these ingredients will be present in an amount effective to accomplish its purpose. Generally, these optional ingredients are included individually at an amount of up to 5% (by weight based on the total weight of the composition).

Packaging and Dosing

A laundry detergent composition of the invention may be packaged as unit doses in polymeric film soluble in the wash water. Alternatively, the detergent composition of the invention may be supplied in multidose plastics packs with a top or bottom closure. A dosing measure may be supplied with the pack either as a part of the cap or as an integrated system.

A method for the laundering of fabric stains using a laundry detergent composition according to the invention comprises diluting a dose of the laundry detergent composition to obtain a wash liquor, and washing the stained fabric with the wash liquor so formed.

The method may suitably be carried out in a top-loading or front-loading automatic washing machine, or can be carried out by hand.

In automatic washing machines, the dose of laundry detergent composition is typically put into a dispenser and from there it is flushed into the machine by the water flowing into the 5 machine, thereby forming the wash liquor. Dosages for a typical front-loading washing machine (using 10 to 15 litres of water to form the wash liquor) may range from about 10 ml to about 100 ml, preferably about 15 to 75 ml. Dosages for a typical top-loading washing machine (using from 40 to 60 litres of water to form the wash liquor) may be higher, e.g. 100 ml or more. Lower dosages of detergent (e.g. 50 ml or less) may be 10 used for hand washing methods (using about 1 to 10 litres of water to form the wash liquor).

A subsequent aqueous rinse step and drying the laundry is preferred. Any input of water during any optional rinsing step(s) is not included when determining the volume of the wash liquor. Laundry drying can take place either in an automatic dryer or in the open air.

The invention will now be further described with reference to the following non-limiting Examples.

EXAMPLES

All weight percentages are by weight based on total weight unless otherwise specified.

Synthesis of Itaconate Surfactant of Formula (I) According to the Invention

Step 1—Synthesis of monolauryl itaconate

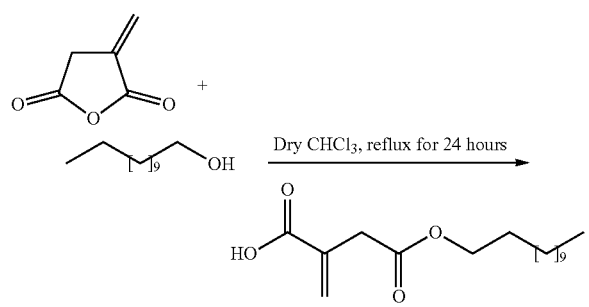

Itaconate anhydride (10 g, 76.9 mmol) and lauryl alcohol (17.1 g, 92.3 mmol) were dissolved in 100 ml of dry chloroform and refluxed overnight (16 h). The reaction mixture was concentrated with minimum amount of chloroform followed by addition of hexane afforded white precipitate which was filtered. The white precipitate was collected and dried in vacuum.

Step 2—Synthesis of PEG-tosylate:

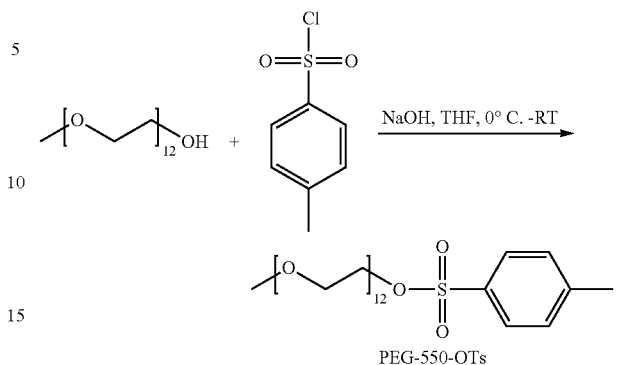

NaOH (2.2 g, 54.5 mmol) was dissolved in a minimum amount of water (2-3 ml) and added to the solution of PEG-500 (20 g, 36.6 mmol) in THF (100 ml). The reaction mixture was cooled to 0° C. followed by slow addition of tosyl chloride (10.4 g, 54.5 mmol) and the reaction mixture allowed to come to room temperature. The reaction mixture was stirred at room temperature for 24 h followed by addition of water (20 ml). The reaction mixture was stirred for 30 min and the THF layer was collected and passed through anhydrous sodium sulphate. The liquid thus obtained was dissolved in diethyl ether to remove excess p-toluene sulfonic acid (white solid precipitates out); the ether layer was evaporated to dryness to obtain a pure product.

Step 3—Synthesis of C12-Ita-PEG-550

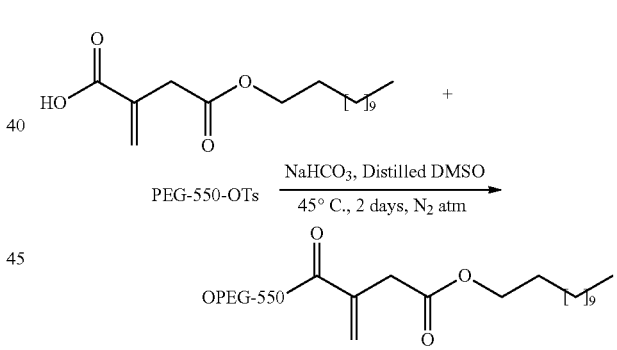

Monolauryl itaconate from step 1 (5.4 g, 17.3 mmol), PEG-550-tosylate from step 2 (11.1 g, 15.8 mmol), NaHCO$_3$ (2.6 g, 31.6 mmol) and KI (catalytic amount) were dissolved in a minimum amount of DMSO (5 ml) and stirred at 40° C. for 2 days.

C16-Ita-PEG-550 may be made by following steps 1 to 3 above with the substitution of cetyl alcohol for the lauryl alcohol in step 1.

Efficacy in Stain Removal of Itaconate Surfactants of Formula (I) According to the Invention Itaconate surfactants of formula (I) according to the invention were evaluated for their stain removal performance on a variety of standard stains (baby food, grass and mud, tomato puree, red wine, garden soil, beef fat, chocolate ice cream and black tea) on cotton and polyester fabrics.

A series of surfactant mixtures were prepared with ingredients and ratios as shown below in Table 1:

TABLE 1

| Ingredient | wt.% (active ingredient) Formulation | | | |
|---|---|---|---|---|
| | Ex.A | Ex.B | Ex.1 | Ex.2 |
| LAS acid | 5 | | | |
| alcohol ethoxylate | 5 | | | |
| SLES | 5 | | | |
| Polyoxyethylene (20) sorbitan monolaurate | | 7.5 | 5 | 5 |
| Polyoxyethylene (4) sorbitan monolaurate | | 7.5 | 5 | 5 |
| C12-Ita-PEG-550 | | | 5 | |
| C16-Ita-PEG-550 | | | | 5 |
| water | q.s. to 100 | | | |

Examples A and B are comparative examples (not according to the invention). Examples 1 and 2 are Examples according to the invention.

Polyester test fabrics and cotton test fabrics stained with the above standard stains were washed with the surfactant mixtures shown in Table 1. The extent of stain removal was measured by making diffuse reflectance measurements using a spectrometer, and expressed as the Stain Removal Index (SRI), defined as:

$$SRI = 100 - \Delta E$$, where $\Delta E$ is the difference in colour of the stained test fabric compared to the unstained test fabric.

A higher SRI value indicates cleaner fabric.
The results are shown in Table 2.

TABLE 2

| Test stain/fabric | Stain removal index (SRI) Test formulation | | | |
|---|---|---|---|---|
| | A | B | 1 | 2 |
| baby food/cotton | 87 | 93 | 86 | 86 |
| grass and mud/cotton | 78 | 77 | 78 | 78 |
| tomato puree/cotton | 81 | 82 | 80 | 80 |
| red wine/cotton | 92 | 87 | 91 | 86 |
| garden soil/polyester | 94 | 94 | 94 | 92 |
| beef fat/polyester | 96 | 92 | 93 | 91 |
| chocolate ice cream/polyester | 98 | 96 | 99 | 98 |
| black tea/polyester | 96 | 92 | 98 | 98 |

The results show that Examples 1 and 2 provide parity performance (ΔSRI: +/−2.5) against most of the standard stains when compared with Examples A and B, and improved performance (ΔSRI>+/−2.5) for certain polyphenolic stains, such as red wine, chocolate ice cream and black tea (especially when compared with Example B).

The following Examples 3 to 5 illustrate laundry detergent compositions according to the invention.

| Ingredient | wt.% (active ingredient) Formulation | | |
|---|---|---|---|
| | Example 3 | Example 4 | Example 5 |
| LAS acid | 10 | 6 | 10 |
| alcohol ethoxylate | 5 | 3 | 5 |
| zeolite builder | 20 | | |
| sodium carbonate | 20 | | |
| enzymes | 1 | 1 | 2 |
| whitening agent | 0.1 | 0.1 | 0.1 |
| sodium percarbonate | 15 | | |
| TAED | 1 | | |
| itaconate surfactant of formula (I) | 1.5 | 9 | 10 |
| HEDP | 1 | 0.5 | 0.5 |
| sodium chloride | | 2 | 2 |
| sodium hydroxide | | 1 | 1 |
| dispersants | | 1 | 2 |
| water, minors | q.s. to 100 | | |

The invention claimed is:

1. An itaconate surfactant having the following formula (I)

$$R^1\text{—}O\text{—}C(=O)\text{—}C(=CH_2)\text{—}CH_2\text{—}C(=O)\text{—}O\text{—}[CH_2CH_2O]_n\text{—}R^2 \quad (I)$$

in which $R^1$ is selected from aliphatic hydrocarbyl groups having 4 to 22 carbon atoms;
$R^2$ is selected from hydrogen and aliphatic hydrocarbyl groups having 1 to 4 carbon atoms;
and n is an integer ranging from 8 to 20.

2. The surfactant according to claim 1, in which $R^1$ in formula (I) is selected from linear alkyl or linear alkenyl groups containing from 12 to 18 carbon atoms and 0 or 1 double bond.

3. The surfactant according to claim 1, in which $R^2$ in formula (I) is methyl.

4. The surfactant according claim 1, in which n in formula (I) ranges from 8 to 10.

5. A process for making the itaconate surfactant of formula (I) according to claim 1, the process comprising the steps of:
(i) reacting itaconate anhydride with an alcohol of the general formula $R^1OH$ to yield an itaconate ester, in which $R^1$ is selected from aliphatic hydrocarbyl groups having 4 to 22 carbon atoms; and
(ii) ethoxylating the itaconate ester to produce the itaconate surfactant of formula (I).

6. The process according to claim 5, comprising the steps of:
(i) reacting itaconate anhydride with an alcohol of the general formula $R^1OH$ to yield an itaconate ester, in which $R^1$ is selected from aliphatic hydrocarbyl groups having 4 to 22 carbon atoms;
(iia) reacting polyethylene glycol of the formula $R^2O\text{—}(CH_2CH_2O)_n\text{—}CH_2CH_2OH$ with a sulfonyl halide, to form an intermediate; in which $R^2$ is selected from hydrogen and aliphatic hydrocarbyl groups having 1 to 4 carbon atoms; and
(iib) reacting the itaconate ester obtained in (i) with the intermediate obtained in (iia) to produce the itaconate surfactant of formula (I).

7. A laundry detergent composition including from 0.5 to 35% by weight based on the total weight of the composition of an itaconate surfactant according to claim 1.

* * * * *